(12) United States Patent
Cai et al.

(10) Patent No.: US 8,486,657 B2
(45) Date of Patent: Jul. 16, 2013

(54) ANTI-PREPROPROTEIN AND ANTI-PREPROTEIN ANTIBODIES AS IMMUNOHISTOCHEMICAL MARKERS

(76) Inventors: Xiaohong Cai, Portland, OR (US); Thomas Cai, Portland, OR (US)

(*) Notice: Subject to any disclaimer, the term of this patent is extended or adjusted under 35 U.S.C. 154(b) by 339 days.

(21) Appl. No.: 12/728,997

(22) Filed: Mar. 22, 2010

(65) Prior Publication Data

US 2011/0229912 A1 Sep. 22, 2011

(51) Int. Cl.
| | |
|---|---|
| C07K 16/18 | (2006.01) |
| C07K 16/42 | (2006.01) |
| C12Q 1/28 | (2006.01) |
| G01N 33/53 | (2006.01) |
| G01N 33/533 | (2006.01) |
| G01N 33/534 | (2006.01) |
| G01N 33/535 | (2006.01) |
| G01N 33/543 | (2006.01) |
| G01N 33/554 | (2006.01) |
| G01N 33/563 | (2006.01) |
| G01N 33/567 | (2006.01) |
| G01N 33/577 | (2006.01) |
| C12P 21/08 | (2006.01) |

(52) U.S. Cl.
USPC ....... 435/40.52; 435/7.1; 435/7.21; 435/7.23; 435/7.24; 435/7.5; 435/7.8; 435/7.95; 435/28; 435/40.5; 436/503; 436/504; 436/512; 436/518; 436/519; 436/547; 436/548; 436/164; 436/172; 436/813; 530/387.9; 530/388.2; 530/388.25; 530/388.73; 530/388.8; 530/389.3; 530/389.6; 530/389.7; 530/391.1; 530/391.3

(58) Field of Classification Search
USPC ................. 435/7.1, 7.21, 7.23, 7.24, 7.5, 7.8, 435/7.95, 28, 40.5, 40.52, 975; 436/503, 436/504, 512, 518, 519, 547, 548, 164, 172, 436/813; 530/327, 328, 388.2, 388.25, 388.73, 530/388.8, 389.3, 389.6, 389.7, 391.1, 391.3, 530/387.9
See application file for complete search history.

(56) References Cited

U.S. PATENT DOCUMENTS

2005/0186658 A1* 8/2005 Gupta et al. .................. 435/69.1
2009/0214550 A1* 8/2009 Sahin et al. .................. 424/139.1

OTHER PUBLICATIONS

Furuta et al., 2002. preprodynorphin-, preproenkephalin-, preprotachykinin A-, and preprotachkinin B-immunoreactive neurons in the accumbens nucleus and olfactory tubercle: double-immunofluorescence anaylsis. Neuroscience 114: 611-627.*
Hashimoto et al., 1997. Antigenicity of pro-osteocalcin in hard tissue: the authenticity to visualize osteocalcin-producing cells. J. Bone Mineral Metab. 15: 122-131.*
Stanton et al., 1991. Processing of prothrombin in the secretory pathway. Biochem. J. 277: 59-65.*
Bahrami et al., "Undifferentiated tumor: true identity by immunohisotchemistry," *Arch Pathol Lab Med.* 132:326-348, 2008.
Bin et al., "The hexa- and pentapeptide extension of proalbumin I. Chemical synthesis of serum albumin propeptides," *Biochimica et Biophysica Acta* 670:421-3, 1981.
Higgins et al., "Application of immunohistochemistry in the diagnosis of Non-Hodgkin and Hodgkin's lymphoma," *Arch Pathol Lab Med.* 132:441-461, 2008.
Jagirdar, "Immunohistochemistry then and now," *Arc. Pathol Lab Med.* 132:323-325, 2008.
Krishna et al., "Detection of albumin messenger RNA in hepatic and extrahepatic neoplasms: A marker of hepatocellular differentiation," *Am J Surg. Path.* 21:147-52, 1997.
Krishna, "Diagnosis of metastatic neoplasms: An immunohistochemical approach," *Arch. Pathol Lab Med.* 134:207-15, 2010.
Minghetti et al., "Molecular structures of the human albumin gene is revealed by nucleotide sequence within q11-22 of chromosome 4," *J Bio. Chem.* 261:6747-57, 1986.
Oda et al., "Production of propeptide-directed antibody: its application to the purification of proalbumin and analysis of proalbumin processing," *J Biochem* 108:549-53, 1990.
Weigand et al., "The hexa- and pentapeptide extension of proalbumin II. Processing of specific antibodies against the synthetic hexapeptide," *Biochimica et Biophysica Acta* 670:424-7, 1981.

* cited by examiner

*Primary Examiner* — Mark Shibuya
*Assistant Examiner* — James L Grun
(74) *Attorney, Agent, or Firm* — Klarquist Sparkman, LLP

(57) ABSTRACT

It is disclosed herein that antibodies specific for preproproteins or preproteins, which are synthesized by certain types of cells or tissues, can be used in immunohistochemistry assays to discriminate between the intracellular component of the protein (including the preproprotein, preprotein and/or proprotein forms of the protein) from the secreted component of the same protein. Accordingly, provided herein is an immunohistochemical method for specific detection of the intracellular form of a protein in a biological sample using an antibody specific for the preproprotein or preprotein form of the protein. In particular examples, the protein is albumin or an immunoglobulin light chain. Also disclosed herein are preproprotein-specific ore preprotein-specific antibodies that can be used to detect specific cell types, tissue lesions or other pathological foci and metastases by IHC. In particular, antibodies that specifically bind human preproalbumin, but do not bind the secreted form of albumin are disclosed.

19 Claims, No Drawings

ANTI-PREPROPROTEIN AND ANTI-PREPROTEIN ANTIBODIES AS IMMUNOHISTOCHEMICAL MARKERS

FIELD

This disclosure concerns antibodies specific for prepeproteins or preproteins and their use in immunohistochemistry.

BACKGROUND

When a patient is suspected of having a tumor, a piece of tissue from the suspected site is removed surgically by a physician and is sent to an anatomic pathology laboratory for examination. Typically, the suspected tissue is fixed in formalin, processed in graded alcohols and xyline, embedded in paraffin, sliced into sections with a microtome and stained with hematoxylin-eosin (H&E). The pathologist then examines the stained tissue slides microscopically. Based on the distinct features of the parenchymal and stromal cells in the tissue, the pathologist then makes a diagnosis.

The H&E technique has proven to be one of the most durable in medicine and has remained essentially unchanged for over half a century. It is relatively quick, inexpensive, and suitable for most situations. Most important, it allows an accurate microscopic diagnosis of a large majority of sampled tissues. However, H&E staining has limited applicability in certain situations. For example, H&E staining is insufficient for etiologic, histogenetic or pathogenetic inquiries. Using the H&E technique, a pathologist can usually make a diagnosis of malignancy or benignicity. However, it is difficult, if not impossible, to identify the line of differentiation of the tumor. As a consequence, pathologists have always searched for additional techniques to probe those questions because identification of the line of differentiation of the tumor is crucial for the tumor's management. For instance, a poorly differentiated malignancy with B lymphocytic differentiation and CD20 positivity could be curable with RITUXAN™.

Another technique used by pathologists is immunohistochemistry (IHC). This technique was introduced 50 years ago for detection of antigens in frozen tissue with immunofluorescence. The science of antigen detection with visibly tagged antibodies did not come to life until the advent of monoclonal antibodies in the 1980s. In combination with an improved detection system, antigen epitope retrieval and automation, IHC is now an essential part of an anatomic pathology laboratory. It can be used to detect virtually any immunogenic molecule with remarkable sensitivity and specificity. It can also be evaluated against the morphologic backgrounds with which pathologists have long been familiar. With current IHC techniques, approximately 90% of the tumors with diagnostic difficulties by H&E technique can be accurately classified.

One of the crucial aspects of IHC is to have tumor-specific, tissue-specific or cell lineage-specific antibodies. Although all of our tissues and cells come from a single stem cell, during tissue differentiation different tissues and cells may have different antigenic profiles. For instance, thyroid transcription factor (TTF-1) is a nuclear protein transcription factor selectively expressed during embryogenesis in the thyroid, the diencephalon of the brain and respiratory epithelium. It is found only in thyroid tumors regardless of histologic types, as well as in lung carcinoma. The utility of TTF-1 becomes readily apparent in the differential diagnosis of primary versus metastatic carcinomas, especially in the lung or in pleural effusions.

SUMMARY

It is disclosed herein that antibodies specific for the preproprotein or preprotein form of a selected protein can be used for immunohistochemistry assays to specifically detect the intracellular and/or membrane forms (which includes preprotein, preproprotein and proprotein forms) of a protein without high background staining that can result from cross-reactivity with the secreted form of the protein. Accordingly, provided herein is an immunohistochemical method for specific detection of the intracellular form of a protein in a biological sample. In some embodiments, the method includes (i) contacting the sample with an antibody raised against the preproprotein or preprotein form of the protein, wherein the antibody specifically binds the intracellular form of the protein and does not bind the secreted form of the protein; and (ii) detecting the presence of the antibody bound to the protein, thereby specifically detecting the intracellular form of the protein in the sample. In particular examples, the protein is albumin or an immunoglobulin light chain. Further provided are antibodies that specifically bind human preproalbumin, but do not bind the secreted form of albumin.

The foregoing and other objects, features, and advantages of the invention will become more apparent from the following detailed description.

SEQUENCE LISTING

The amino acid sequences listed in the accompanying sequence listing are shown using standard three letter code for amino acids, as defined in 37 C.F.R. §1.822. In the accompanying sequence listing:

SEQ ID NO: 1 is the amino acid sequence of a preproalbumin peptide.

SEQ ID NO: 2 is the amino acid sequence of human preproalbumin.

SEQ ID NOs: 3-29 are the amino acid sequences of the prepeptides of human immunoglobulin kappa light chains.

SEQ ID NOs: 30-39 are the amino acid sequences of the prepeptides of human immunoglobulin lambda light chains.

SEQ ID NO: 40 is the amino acid sequence of a proalbumin peptide.

DETAILED DESCRIPTION

I. Introduction

It is disclosed herein that antibodies directed to preproproteins, which are synthesized by certain types of cells or tissues, can be used immunohistochemically to discriminate the intracellular component from the secreted component of the same protein. Therefore, disclosed herein are preproprotein-specific antibodies that can be used to detect specific cell types, tissue lesions or other pathological foci and metastases by IHC without background staining of secreted proteins or serum proteins.

II. Abbreviations

BSA Bovine serum albumin
CDR Complementarity determining region
H&E Hematoxylin-eosin
ELISA Enzyme-linked immunosorbent assay
IHC Immunohistochemistry
KLH Keyhole limpet hemocyanin
PBS Phosphate buffered saline III. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"), which are examples of antigen-binding antibody fragments. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a particular antigen will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "human" antibody (also called a "fully human" antibody) is an antibody that includes human framework regions and all of the CDRs from a human immunoglobulin. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Antigen: A molecule that stimulates an immune response. Antigens are usually proteins or polysaccharides. An epitope is an antigenic determinant. These are particular chemical groups or peptide sequences on a molecule that are antigenic, such that they elicit a specific immune response. An antibody binds a particular antigenic epitope. The binding of an antibody to a particular antigen or epitope of an antigen can be used (such as in an IHC assay) to localize the position of the antigen for example in or on a biological sample, or determine if the particular antigen is present in a biological sample. For example, to detect a particular antigen of interest, the primary antibody used in the IHC assay specifically binds to the antigen.

Antigen retrieval: A process for recovering antigenicity in fixed processed tissue samples. Antigen retrieval is also sometimes referred to as epitope retrieval, target retrieval, or target unmasking. Various methods are used for antigen retrieval, including heat treatment, protease digestion, or a combination of heat and protease treatment. Methods of antigen retrieval for use with IHC have been previously described (see, for example PCT Publication No. WO 2009/110936 and U.S. Patent Application Publication No. 2006/0134793).

Antigen-specific: As used herein, an "antigen-specific" antibody is an antibody that was elicited (produced and/or activated) in response to a particular antigen. An "antigen-specific" antibody is capable of binding to the antigen, typically with high affinity.

Avidin/Streptavidin: The extraordinary affinity of avidin for biotin allows biotin-containing molecules in a complex mixture to be discretely bound with avidin. Avidin is a glycoprotein found in the egg white and tissues of birds, reptiles and amphibia. It contains four identical subunits having a combined mass of 67,000-68,000 daltons. Each subunit consists of 128 amino acids and binds one molecule of biotin. Extensive chemical modification has little effect on the activity of avidin, making it especially useful for protein purification.

Another biotin-binding protein is streptavidin, which is isolated from *Streptomyces avidinii* and has a mass of 60,000 daltons. In contrast to avidin, streptavidin has no carbohydrate and has a mildly acidic pI of 5.5. Another version of avidin is NEUTRAVIDIN™ Biotin Binding Protein (available from Pierce Biotechnology) with a mass of approximately 60,000 daltons.

The avidin-biotin complex is the strongest known non-covalent interaction ($K_a = 10^{15}$ $M^{-1}$) between a protein and ligand. The bond formation between biotin and avidin is very rapid, and once formed, is unaffected by extremes of pH, temperature, organic solvents and other denaturing agents.

Although examples disclosed herein use streptavidin as a specific binding agent, the streptavidin could be substituted with other types of avidin. The term "avidin" is meant to refer to avidin, streptavidin and other forms of avidin (such as derivatives or analogs thereof) that have similar biotin binding characteristics. Analogs or derivatives of avidin/streptavidin include, but are not limited to, nitro-streptavidin, non-glycosylated avidin, N-acyl avidins (such as N-acetyl, N-phthalyl and N-succinyl avidin), and the commercial products EXTRAVIDIN™ (Sigma-Aldrich), Neutralite Avidin (SouthernBiotech) and CaptAvidin (Invitrogen). Additional avidin/streptavidin analogs and derivatives are known in the art (see, for example, U.S. Pat. No. 5,973,124 and U.S. Patent Application Publication Nos. US 2004/0191832; US 2007/0105162; and US 2008/0255004).

Binding affinity: Affinity of an antibody for an antigen. Affinity can be calculated by a modification of the Scatchard method described by Frankel et al., *Mol. Immunol.*, 16:101-106, 1979. Binding affinity can also be measured by an antigen/antibody dissociation rate. In other cases, binding affinity is measured by a competition radioimmunoassay or by ELISA.

Biological sample: As used herein, a "biological sample" refers to a sample obtained from a subject (such as a human or veterinary subject). In particular examples of the methods disclosed herein, the biological sample is a tissue sample, such as from a biopsy. Biological samples from a subject include, but are not limited to, tissue samples and cell samples. Biological samples can also refer to serum, blood, plasma, urine, saliva, cerebral spinal fluid (CSF) or other bodily fluid samples.

Biotin: A molecule (also known as vitamin H or vitamin $B_7$) that binds with high affinity to avidin and streptavidin. Biotin is often used to label nucleic acids and proteins for subsequent detection by avidin or streptavidin linked to a detectable label, such as a fluorescent or enzymatic reporter molecule. Biotinylation of a molecule (such as an antibody or other protein sample) is routinely achieved in the art by reacting a free carboxyl group on biotin with an amine group on a protein, such as an amine group found in an antibody or protein analyte/analog. Unless indicated otherwise, the term "biotin" includes derivatives or analogs that participate in a binding reaction with avidin. Biotin analogs and derivatives include, but are not limited to, N-hydroxysuccinimide-iminobiotin (NHS-iminobiotin), amino or sulfhydryl derivatives of 2-iminobiotin, amidobiotin, desthiobiotin, biotin sulfone, caproylamidobiotin and biocytin, biotinyl-ε-aminocaproic acid-N-hydroxysuccinimide ester, sulfo-succinimide-iminobiotin, biotinbromoacetylhydrazide, p-diazobenzoyl biocytin, 3-(N-maleimidopropionyl)biocytin, 6-(6-biotinamidohexanamido)hexanoate and 2-biotinamidoethanethiol. Biotin derivatives are also commercially available, such as DSB-X™ Biotin (Invitrogen). Additional biotin analogs and derivatives are known in the art (see, for example, U.S. Pat. No. 5,168,049; U.S. Patent Application Publication Nos. 2004/0024197, 2001/0016343, and 2005/0048012; and PCT Publication No. WO 1995/007466).

Carrier: A molecule to which an antigen can be bound. Carrier molecules include immunogenic carriers and specific-binding carriers. When bound to an immunogenic carrier, the bound molecule may become immunogenic or more immunogenic. Immunogenic carriers may be chosen to increase the immunogenicity of the bound molecule and/or to elicit antibodies against the carrier, which are diagnostically, analytically, and/or therapeutically beneficial. Covalent linking of a molecule to a carrier can confer enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups, for example primary and/or secondary amino groups, azido groups, hydroxyl groups, or carboxyl groups, to which a reactant moiety can be attached. Bacterial products and viral proteins (such as hepatitis B surface antigen and core antigen) can be used as carriers, as well as proteins from higher organisms, such as keyhole limpet hemocyanin (KLH), horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide). The carrier can be water soluble or insoluble, and can be a protein or polypeptide. Carriers that fulfill these criteria are generally known in the art (see, for example, Fattom et al., *Infect. Immun.* 58:2309-2312, 1990; Devi et al., *Proc. Natl. Acad. Sci. USA* 88:7175-7179, 1991; Szu et al., *Infect. Immun.* 59:4555-4561, 1991; Szu et al., *J. Exp. Med.* 166:1510-1524, 1987; and Pavliakova et al., *Infect. Immun.* 68:2161-2166, 2000). In some embodiments, the carrier is KLH.

Conjugated: Refers to two molecules that are bonded together, for example by covalent bonds. An example of a conjugate is a molecule (such as an antibody) conjugated to a detectable label, such as a fluorophore or enzyme.

Contacting: Placement in direct physical association; includes both in solid and liquid form. As used herein, "contacting" is used interchangeably with "exposed."

Control: A reference standard, for example a positive control or negative control. A positive control is known to provide a positive test result. A negative control is known to provide a negative test result. However, the reference standard can be a theoretical or computed result, for example a result obtained in a population.

Detect: In the context of the present disclosure, "detect" or "detection" refers to determining if an agent (such as a signal or particular antigen or protein) is present or absent in a sample, such as by using IHC. In some examples, this can further include quantification.

Detectable label: A detectable compound or composition that is attached directly or indirectly to another molecule, such as an antibody or a protein, to facilitate detection of that molecule. Specific, non-limiting examples of labels include fluorophores, enzymes, and radioactive isotopes.

Detection molecule: As used herein, a "detection molecule" is a molecule that can be used in an IHC assay as a means to detect the presence of an antigen-antibody-secondary antibody complex. In the context of the present disclosure, a detection molecule comprises a specific binding partner fused to a detectable label. Examples of specific binding partners include, for example, biotin and avidin. The detection molecule works by binding to a secondary antibody that is conjugated to a corresponding specific binding partner. In some examples, the secondary antibody is conjugated to biotin and the detection molecule includes streptavidin bound to a label (such as peroxidase).

Diagnostic: A diagnostic method is a method for identifying the presence or nature of a pathologic condition, such as cancer.

Epitope: An antigenic determinant. These are particular chemical groups or peptide sequences on a molecule that are antigenic, i.e. that elicit a specific immune response.

Fixation: A process which preserves cells and tissue constituents in as close to a life-like state as possible and allows them to undergo preparative procedures without change. Fixation arrests the autolysis and bacterial decomposition processes which begin upon cell death, and stabilizes the cellular and tissue constituents so that they withstand the subsequent stages of tissue processing, such as for IHC.

Tissues may be fixed by either perfusion with or submersion in a fixative, such as an aldehyde (such as formaldehyde, paraformaldehyde, glutaraldehyde, and the like). Other fixatives include oxidizing agents (for example, metallic ions and complexes, such as osmium tetroxide and chromic acid), protein-denaturing agents (for example, acetic acid, methanol, and ethanol), fixatives of unknown mechanism (for example, mercuric chloride, acetone, and picric acid), combination reagents (for example, Carnoy's fixative, methacarn, Bouin's fluid, B5 fixative, Rossman's fluid, and Gendre's fluid), microwaves, and miscellaneous (for example, excluded volume fixation and vapour fixation). Additives may also be included in the fixative, such as buffers, detergents, tannic acid, phenol, metal salts (for example, zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin).

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) can eliminate the need for an external source of electromagnetic radiation, such as a laser.

Examples of particular fluorophores that can be used in the methods disclosed herein are provided in U.S. Pat. No. 5,866, 366 to Nazarenko et al., such as 4-acetamido-4'-isothiocyanatostilbene-2,2'disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N, N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC™ (Applied Biosystems), LC Red 640, LC Red 705, Yakima yellow amongst others. Other suitable fluorophores include those known to those skilled in the art, for example those available from Life Technologies (Carlsbad, Calif.).

Immunohistochemistry (IHC): A method of determining the presence or distribution of an antigen in a sample by detecting interaction of the antigen with a specific binding agent, such as an antibody. IHC is widely used in clinical and diagnostic applications, such as to diagnose particular disease states or conditions. For example, a diagnosis of a particular type of cancer can be made based on the presence of a particular marker molecule present in a sample obtained from a subject. IHC is also widely used in basic research to understand the distribution and localization of biomarkers in different parts of a tissue.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A label is an agent placed on a target to directly or indirectly render it detectable. Hence the label can be a component applied to the target that subsequently binds a detectable agent. A "detectable label" is a detectable compound or composition that is conjugated directly or indirectly to another molecule, such as an antibody or a protein, to facilitate detection of that molecule. Specific, non-limiting examples of detectable labels include fluorescent tags, enzymatic linkages, and radioactive isotopes. In some embodiments, the detectable label is a detectable marker conjugated to a biotin-binding agent, such as avidin or streptavidin (for example, streptavidin conjugated to a fluorescent marker or enzyme that can be detected by optical or colorimetric methods). "Labeling" refers to the act of linking a label to a molecule of interest, for example linking to the molecule of interest a component that subsequently binds a detectable label or linking a detectable label itself to the molecule of interest, or both. Various methods of labeling polypeptides and other molecules are known in the art and may be used. Examples of detectable labels for polypeptides include, but are not limited to, the following: radioisotopes or radionucleotides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, chromophores (such as horseradish peroxidase or alkaline phosphatase), biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates.

Linker: In some cases, a linker is a peptide within an antibody binding fragment (such as an Fv fragment) which serves to indirectly bond the variable heavy chain to the variable light chain. "Linker" can also refer to a peptide serving to link two different proteins, such as an antibody and a detectable label, or one member of a specific binding pair to a detectable label.

The terms "conjugating," "joining," "bonding" or "linking" refer to making two polypeptides into one contiguous polypeptide molecule, or to covalently attaching a radionuclide or other molecule to a polypeptide, such as an antibody. In the specific context, the terms include reference to joining a ligand, such as an antibody moiety, to a detectable label. The linkage can be either by chemical or recombinant means. "Chemical means" refers to a reaction between the two molecules such that there is a covalent bond formed between the two molecules to form one molecule.

Neoplasia, malignancy, cancer or tumor: The result of abnormal and uncontrolled growth of cells. Neoplasia, malignancy, cancer and tumor are often used interchangeably. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Preproproteins, preproteins, proproteins and secreted proteins: A "preprotein" is the form of a protein that contains a signal sequence that specifies its insertion into or through membranes. A "proprotein" is a protein that is inactive, the full function is only present when an inhibitory sequence has been removed by proteolysis. A "preproprotein" has both sequences still present and is the precursor of a proprotein. A "secreted protein" is a protein that is exported through the cytoplasmic membrane. As used herein, an "intracellular form" or "intracellular/membrane form" of a protein is the component of a particular protein that is found intracellularly or within the membrane of a cell. Thus, the intracellular and/or membrane forms of a protein include preprotein and proprotein forms of the protein. The secreted form of a protein (in some cases referred to as "mature" proteins) has been post-translationally modified to remove the signal sequence and is thus secreted outside the cell.

Purified: The term purified does not require absolute purity; rather, it is intended as a relative term. Thus, for example, a purified protein preparation (such as an antibody preparation) is one in which the peptide or protein is more enriched than the peptide or protein is in its natural environment within a cell. In one embodiment, a preparation is purified such that the protein or peptide represents at least 50% of the total peptide or protein content of the preparation. A substantially purified protein is at least 60%, 70%, 80%, 90%, 95% or 98% pure. Thus, in one specific, non-limiting example, a purified protein is 90% free of other proteins or cellular components. The antibodies disclosed herein can be purified by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982).

Raised against: An antibody "raised against" a specific protein or peptide is an antibody that is produced following immunization with the specific protein or peptide. In the context of the present disclosure, an antibody raised against a preprotein fragment specifically binds the intracellular component of the protein (the preproprotein and proprotein forms) but does not bind the secreted form of the protein. The preprotein fragment does not contain amino acid sequence from the secreted form of the protein, or does not contain sufficient amino acid sequence from the secreted form to enable binding of a preprotein-specific antibody. Similarly, an antibody raised against a preprotein fragment specifically binds the intracellular component of the protein (the preprotein form) but does not bind the secreted form of the protein (the form lacking the signal sequence of the preprotein). The preprotein fragment does not contain amino acid sequence from the secreted form of the protein, or does not contain sufficient amino acid sequence from the secreted form to enable binding of a preprotein-specific antibody.

Specific binding partner: A member of a pair of molecules that interact by means of specific, non-covalent interactions that depend on the three-dimensional structures of the molecules involved. Exemplary pairs of specific binding partners include antigen/antibody, hapten/antibody, ligand/receptor, nucleic acid strand/complementary nucleic acid strand, substrate/enzyme, inhibitor/enzyme, carbohydrate/lectin, biotin/avidin (such as biotin/streptavidin), and virus/cellular receptor.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

Some secreted proteins are tissue- or cell-specific with a high concentration in the serum. One example of such a secreted protein is albumin. Albumin is a ubiquitous protein that is synthesized only by hepatocytes. Human albumin contains 580 amino acids and the number of albumin molecules produced by a single hepatocyte is estimated to be about 40,000. Since it is only synthesized in hepatocytes, albumin could serve as a marker for hepatocellular differentiation such as hepatocellular carcinoma. However, albumin immunohistochemistry is complicated by an elevated background due to non-specific uptake of albumin by a variety of cells, or more often, staining of extracellular serum or stromal albumin molecules. The staining result is often low in signal and high in noise.

Another example is immunoglobulin. Normal mature B cells produce and export immunoglobulin to the cell surface as an antigen receptor. Normal plasma cells synthesize and secret immunoglobulin into the serum. The immunoglobulin molecule, a heterodimer comprising one light chain and one heavy chain molecule, is unique in each cell. The gene rearrangement process that generates the immunoglobulin molecule results in either a productive kappa gene or a productive lambda gene. The mechanics of the rearrangement process normally produce approximately twice as many kappa-bearing cells as lambda-bearing cells. This ratio is maintained in populations of normal or reactive B cells but is altered in malignant populations. In practice, whenever a B cell or plasma cell population exceeds the normal 2:1 ratio by four-fold (i.e. >85% kappa positive cells or roughly 65% lambda positive cells) malignant B cell lymphoma or malignant plasmacytoma/myeloma is diagnosed. However, light chain immunohistochemistry is complicated by an elevated background due to non-specific uptake of immunoglobulin by a variety of cells, or more often, staining of extracellular serum or stromal immunoglobulin molecules. Therefore, immunoglobulin light chain immunohistochemistry challenges the pathologist with a result that is often low in signal and high in background noise.

All of the secreted proteins in eukaryotes and prokaryotes are synthesized in the form of preprotein. The preprotein is identical to the secreted protein with a single exception—it has an additional polypeptide at its amino terminal end known as the leader or signal peptide. This polypeptide is required for the transport of the preprotein across the endoplasmic reticulum membrane into the lumen of the ER, and is cleaved off as soon as the preprotein moves into the cisternae of the rough ER. Additionally, many secreted proteins have been found to be secreted by cleavage from larger precursor forms containing additional peptide segments. Protein species carrying such peptide segments are termed "pro-proteins." For instance, albumin is synthesized in the liver as preproalbumin, and the leader or signal peptide is cleaved off as the precursor protein (proalbumin) crosses the lumen of the endoplasmic reticulum and enters the cisternae of the rough ER. When proalbumin reaches the Golgi vesicles, it is cleaved off again to remove the propeptide Arg-Gly-Val-Phe-Arg-Arg (amino acids 19-24 of SEQ ID NO: 2). The final product, albumin, is then constitutively secreted into the blood circulation.

This disclosure relates to the production of antibodies directed to preproproteins or preproteins, which are synthesized by special types of cells or tissues, and uses them for IHC to discriminate the intracellular/membrane component from the secreted component of the same protein. Therefore, the disclosed antibodies can be used to detect cell types, tissue lesions or other pathological foci and metastases immunohistochemically without background staining of secreted proteins or serum proteins.

Thus, provided herein is an immunohistochemical method for specific detection of the intracellular form of a protein in a biological sample. In some embodiments, the method comprises (i) contacting the sample with an antibody raised against the preproprotein or preprotein form of the protein, wherein the antibody specifically binds the intracellular form of the protein and does not bind the secreted form of the protein; and (ii) detecting the presence of the antibody bound to the protein, thereby specifically detecting the intracellular form of the protein in the sample.

The disclosed method can be used with any protein that has both intracellular/membrane forms (for example preproprotein or preprotein forms) and secreted forms (in some cases this is the mature form of the protein). In particular embodiments disclosed herein, the protein is albumin or an immunoglobulin light chain. Albumin is an example of a protein that has preproprotein, proprotein and secreted forms. An immunoglobulin light chain is an example of a protein that has preprotein and secreted forms. In some examples, the protein is albumin. The amino acid sequence of preproalbumin is set forth herein as SEQ ID NO: 2. In some examples, the immunoglobulin light chain is a kappa light chain. The amino acid sequences of exemplary preprotein kappa light chains are set forth herein as SEQ ID NOs: 3-29. In other examples, the immunoglobulin light chain is a lambda light chain. The amino acid sequences of exemplary preprotein lambda light chains are set forth herein as SEQ ID NOs: 30-39.

The antibodies used in the disclosed method can be any type of antibody or antigen-binding antibody fragment that specifically binds to the intracellular/membrane form of a protein. In some embodiments, the antibody is a polyclonal antibody. In other embodiments, the antibody is a monoclonal antibody. In yet other embodiments, the antibody is an antigen-binding antibody fragment, such as an Fab fragment, Fab' fragment, F(ab)'$_2$ fragment, scFv fragment, or a dsFv fragment.

The disclosed methods include the step of detecting the presence of the preproprotein-specific or preprotein-specific antibody bound to the protein. The detection step can be accomplished using any one of a number of different methods known in the art and routinely used in IHC assays. For example, in one embodiment, detecting the presence of the antibody bound to the protein comprises detecting a label conjugated to the antibody. In another embodiment, detecting the presence of the antibody bound to the protein comprises (i) contacting the sample with a secondary antibody specific for the preproprotein or preprotein antibody, wherein the secondary antibody in conjugated to a detectable label; and (ii) detecting the presence of the label. In yet another embodiment, detecting the presence of the antibody bound to the protein comprises (i) contacting the sample with a secondary antibody specific for the preproprotein or preprotein antibody, wherein the secondary antibody is conjugated to a first binding partner; (ii) contacting the sample with a detection molecule, wherein the detection molecule comprises a second binding partner fused to a detectable label; and (iii) detecting the presence of the label. In each scenario, either the preproprotein/preprotein antibody, a secondary antibody that binds the preproprotein/preprotein antibody, or a binding partner is conjugated to a detectable label. The presence of the detectable label can then be determined using a method appropriate to the type of label used.

In some embodiments, the detectable label is a fluorophore, enzyme or radioactive isotope. In particular examples, the detectable label is an enzyme, such as, but not limited to horseradish peroxidase, beta-galactosidase, luciferase and alkaline phosphatase.

In embodiments that employ a secondary antibody conjugated to a first binding partner and a detection molecule comprising a second binding partner fused to a detectable label, the first and second binding partners can be any two molecules that specifically bind to each other. In some embodiments, the binding partners are avidin and biotin, or derivatives or analogs thereof.

In some examples, the preproprotein or preprotein antibody is directly labeled with a detectable label, such as a fluorophore or enzyme (such as horseradish peroxidase or alkaline phosphatase). Optionally, a secondary antibody that binds the preproprotein or preprotein antibody and containing a label, such as a fluorophore or enzyme, is added to the tissue section and allowed to incubate for a sufficient length of time to allow the preproprotein/preprotein antibody-secondary antibody reaction to occur, if the primary antibody is bound to the antigen present in the tissue. As another option, a secondary antibody that binds the preproprotein/preprotein antibody and is conjugated to a first specific binding partner, is added to the tissue section and allowed to incubate for a sufficient length of time to allow the preproprotein/preprotein antibody-secondary antibody reaction to occur, then a detection molecule comprising a second specific binding partner fused to a detectable label is added and allowed to incubate for a sufficient length of time to allow the preproprotein/preprotein antibody-secondary antibody-detection molecule reaction to occur, if the primary antibody is bound to the antigen present in the tissue.

Once the label has been linked to the preproprotein or preprotein antibody (direct or indirectly via a secondary antibody or detection molecule) it can be detected, thereby detecting the antigen bound by the preproprotein or preprotein antibody. In examples in which the label is an enzyme, a substrate is applied, which is typically a liquid substrate that is converted by the enzyme into an insoluble colored dye. The colored dye precipitates onto the tissue at the site of the primary antibody. Thus, the presence of a colored end product is indicative of a positive antigen-antibody reaction, and the absence of a colored end product is indicative of a negative antigen-antibody reaction. In examples where the specific binding agent is linked to a fluorophore, the light emitted from the fluorophore is detected, for example using a fluorescent microscope. The tissue is typically examined microscopically to detect the presence of the label and therefore the presence of the antigen of interest (wherein generally the absence of a detectable label is indicative of a negative antigen-antibody reaction).

The biological sample used in the disclosed methods can be any type of sample suitable for IHC. In some embodiments, the biological sample is a tissue sample or a cell sample. In some examples, the sample is a tissue sample obtained from a subject suspected of having a disease, such as cancer. Thus, in some cases, the biological sample is a tissue biopsy taken for the purpose of diagnosing the subject. In some embodiments, the tissue sample is a liver tissue sample.

The immunohistochemical methods disclosed herein can further include additional steps that are routine in the preparation and processing of IHC samples. In some embodiments, the biological sample can optionally be formalin-fixed, paraffin-embedded, deparaffinized, dewaxed, immersed in a hydrogen peroxide solution to block endogenous peroxidase activity, subjected to antigen retrieval, counterstained, or any combination of the above. General methods of performing IHC are known in the art and are within the capabilities of one of ordinary skill in the art.

For example, biological samples that are embedded in paraffin can be dewaxed, for example using a paraffin solvent, such as xylene, or other dewaxing procedure. Procedures for dewaxing biological samples and other manipulations are well known in the art and can be found for example in Woods and Ellis, "Laboratory Histopathology: A Complete Reference," Churchill Livingstone, 1994, and "Histological and Histochemical Methods," 4th edition, John Keirnen, Scion Publishing LTD., 2007.

The biological sample can be affixed to a slide or other substrate appropriate for IHC, such as a glass slide. Methods for affixing a biological sample to a slide are well known in the art and can be found for example in Woods and Ellis, "Laboratory Histopathology: A Complete Reference," Churchill Livingstone, 1994 and "Histological and Histochemical Methods," 4th edition, John Keirnen, Scion Publishing LTD., 2007.

Further provided herein are isolated antibodies that specifically bind the preproprotein or preprotein form of a protein. Antibodies that specifically bind a preproprotein or preprotein do not bind the secreted form of the protein. Such antibodies can be generated by immunizing animals (such as rabbits, mice or rats) with a fragment of a preproprotein preprotein that contains at least a portion of the signal sequence.

In some embodiments, the preproprotein is preproalbumin or the preprotein is an immunoglobulin light chain (a kappa light chain or a lambda light chain). Thus, provided are isolated antibodies that specifically bind preproalbumin and do not bind the secreted form of albumin. Also provided are antibodies that specifically bind the preprotein form of a kappa light chain or a lambda light chain, but do not bind the secreted form the light chain.

In some embodiments in which the antibody is specific for preproalbumin, the antibody is raised against a fragment of preproalbumin comprising the amino acid sequence of SAYSRGVFRR (amino acid residues 2-11 of SEQ ID NO: 1). In other embodiments, the antibody is raised against a peptide comprising the sequence of SEQ ID NO: 1 or consisting of the sequence of SEQ ID NO: 1. In some examples, the antibody is raised against a fragment of preproalbumin fused to a carrier molecule, such as KLH.

The antibodies provided herein can be either polyclonal antibodies or monoclonal antibodies, or antigen-binding fragments thereof. Antigen-binding fragments include, for example, Fab fragments, Fab' fragments, F(ab)'$_2$ fragments, scFv fragments, and dsFv fragments.

The preproprotein or preprotein antibodies can be used in the immunohistochemical methods described herein. When the preproprotein-specific antibody is an antibody specific for preproalbumin, the antibody can be used in an immunohistochemical method to detect or diagnose hepatocellular differentiation, such as hepatocellular carcinoma or hepatocellular adenoma. Anti-preproalbumin antibody cannot distinguish normal liver from liver tumor because both normal liver and liver tumor synthesize preproalbumin. However, a preproalbumin-specific antibody can be used to diagnose a tumor with liver differentiation. For example, if a pathologist identifies a tumor without knowing the origin of tumor, the tumor can be stained immunohistochemically with a panel of antibodies. If the tumor expresses preproalbumin only, a diagnosis of hepatocellular tumor (adenoma or carcinoma) is made.

Thus, provided herein is an immunohistochemical method for diagnosis of a hepatocellular tumor in a subject, comprising (i) contacting a tumor sample obtained from the subject with an antibody raised against preproalbumin, wherein the antibody specifically binds the intracellular form of albumin and does not bind the secreted form of albumin; and (ii) detecting the presence of the antibody bound to intracellular albumin, wherein the presence of the antibody bound to intracellular albumin in the tumor sample indicates the subject has an hepatocellular tumor.

When the preproprotein-specific antibody is specific for the preprotein form of a light chain, the antibody can be used in an immunohistochemical method to detect or diagnose malignant B cell lymphoma or malignant plasmacytoma/myeloma. The diagnosis of lymphoma or a plasma cell tumor is based on the clonality or light chain restriction. Normal or reactive B lymphocytes are polyclonal with mixed lambda and kappa light chains. In contrast, lymphoma/plasma cell tumors are monoclonal or at least oligoclonal and therefore only express one type of light chain (termed light chain restriction). If a pathologist stains a piece of tissue immunohistochemically with kappa and lambda light chain preprotein antibodies in parallel, and if the B lymphocytes or plasma cells show only one type of light chain (or shows predominantly one type of light chain), a lymphoma or plasma cell tumor is diagnosed.

Thus, provided herein is an immunohistochemical method for diagnosis of a B lymphoma or plasma cell tumor in a subject, comprising (i) contacting a first sample obtained from the subject with an antibody raised against a kappa light chain preprotein-specific antibody; (ii) contacting a second sample obtained from the subject with an antibody raised against a lambda light chain preprotein-specific antibody; (iii) detecting the presence of the kappa light chain preprotein-specific antibody in the first sample and the presence of the lambda light chain preprotein-specific antibody in the second sample; and (iv) calculating the ratio of kappa light chain expression to lambda light chain expression in the samples, wherein a four-fold or greater change in the normal kappa to lambda light chain expression of 2:1 in the samples indicates the subject has a B lymphoma or a plasma cell tumor. In some embodiments, kappa light chain expression in 85% or greater of the cells in the sample indicates the subject has a B lymphoma or plasma cell tumor. In some embodiments, lambda light chain expression in 65% or greater of the cells in the sample indicates the subject has a B lymphoma or plasma cell tumor. This method can also be carried out using a single sample if the kappa light chain preprotein-specific and lambda light chain preprotein-specific antibodies use different and distinguishable labels (either directly or via secondary antibodies).

The antibodies disclosed herein can also be used in a method to purify the preproprotein and proprotein forms of a particular protein from a biological sample.

V. Antibody Production

The preparation of polyclonal antibodies is well known to those skilled in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992). An exemplary procedure for producing polyclonal antibodies is described in Examples 1 and 2 below.

The preparation of monoclonal antibodies likewise is conventional (see, for example, Kohler & Milstein, *Nature* 256: 495, 1975; Coligan et al., sections 2.5.1-2.6.7; and Harlow et al. in: *Antibodies: a Laboratory Manual*, page 726, Cold Spring Harbor Pub., 1988). Briefly, monoclonal antibodies can be obtained by injecting mice (or rabbits) with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include, for example, affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

An exemplary protocol for the production of rabbit polyclonal antibodies is provided in the Examples below. General procedures for producing rabbit polyclonal antibodies are also well known in the art.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows (and are therefore referred to herein as "antigen-binding fragments"):

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Natl. Acad. Sci. U.S.A.* 69:2659, 1972). Alternatively, the variable chains can be linked by an intermolecular disulfide bond or cross-linked by chemicals such as glutaraldehyde (see, for example, Sandhu, *Crit. Rev. Biotech.* 12:437, 1992). In particular examples, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, *Crit. Rev. Biotech.* 12:437, 1992).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), ovalbumin (OVA) and tetanus toxoid. The coupled peptide is then used to immunize the animal (e.g., a mouse, rat, or rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

Binding affinity for a target antigen is typically measured or determined by standard antibody-antigen assays, such as competitive assays, saturation assays, or immunoassays such as ELISA or radioimmunoassay (RIA). Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is, for example <1 µM, <100 nM, or <0.1 nM. Antibody molecules will typically have a $K_D$ in the lower ranges. $K_D$=[Ab-Ag]/[Ab][Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

For use in the IHC methods disclosed herein, diagnostic or detection moieties (referred to herein as "detectable labels") can be linked to an antibody using any number of means known to those of skill in the art. Exemplary detectable labels include, but not limited to, radiolabels, fluorescent markers, or proteins with enzymatic activity (e.g. horseradish peroxidase, beta-galactosidase, luciferase, alkaline phosphatase). Both covalent and noncovalent attachment means may be used. The procedure for attaching a detectable label to an antibody varies according to the chemical structure of the molecule. Polypeptides typically contain a variety of functional groups, e.g., carboxylic acid (COOH), free amine (—$NH_2$) or sulfhydryl (—SH) groups, which are available for reaction with a suitable functional group on an antibody to result in the binding of the detectable label. Alternatively, the antibody is derivatized to expose or attach additional reactive functional groups. The derivatization may involve attachment of any of a number of linker molecules such as those available from Pierce Chemical Company (Rockford, Ill.). The linker can be any molecule used to join the antibody to the detectable label. The linker is capable of forming covalent bonds to both the antibody and to the detectable label. Suitable linkers are well known to those of skill in the art and include, but are not limited to, straight or branched-chain carbon linkers, heterocyclic carbon linkers, or peptide linkers. Where the antibody and the detectable label are polypeptides, the linkers may be joined to the constituent amino acids through their side groups (e.g., through a disulfide linkage to cysteine) or to the alpha carbon amino and carboxyl groups of the terminal amino acids.

In view of the large number of methods that have been reported for attaching a variety of detectable labels and other agents to antibodies, one skilled in the art will be able to determine a suitable method for attaching a given agent to an antibody or other polypeptide.

The following examples are provided to illustrate certain particular features and/or embodiments. These examples should not be construed to limit the disclosure to the particular features or embodiments described.

EXAMPLES

Example 1

Proalbumin Antibodies are Ineffective for Immunohistochemistry

Although the inventor is unaware of any anti-preprotein antibodies that have been described in the art, two anti-proprotein antibodies have been generated, both of which are specific for anti-proalbumin. Weigand et al. (*Biochim Biophys Acta* 670:424-427, 1981) synthesized the proalbumin hexapeptide and then conjugated this hexapeptide with carbodiimide. Subsequently, rabbits were immunized with the hexapeptide conjugate. The sera from these immunized rabbits showed specificity against the hexapeptide by immunodiffusion and ELISA. No antibody affinity purification nor immunohistochemistry against hepatic tissue were undertaken by Weigand et al. In addition, Oda et al. (*J. Biochem.* 108:549-553, 1990) conjugated the proalbumin peptide to ovalbumin through an additional cysteine residue at the carboxyl terminus. This proalbumin-ovalbumin conjugate was injected into rabbits. Polyclonal antibodies were purified on a proalbumin-coupled affinity column. The polyclonal antibody was used successfully to purify proalbumin from rat liver microsomes and to analyze the proteolytic processing of proalbumin in primary cultured rat hepatocytes. However, no immunohistochemistry against frozen or paraffin-embedded tissue was performed.

The antibodies described by Weigand et al. and Oda et al. are polyclonal and were generated more than 20 years ago. They are not currently available, and to the inventor's knowledge have not been used immunohistochemically for human tissue or lesion diagnosis. To determine whether proalbumin antibodies would useful for immunohistochemistry applications, anti-proalbumin antibody was generated following the methods described by Oda et al., with slight modifications. Briefly, proalbumin peptide (RGVFRRC; SEQ ID NO: 40) was synthesized and purified by high-pressure liquid chromatography (HPLC) with a purity of greater than 90%. The peptide was conjugated to ovalbumin and the conjugate was injected to two rabbits. The polyclonal antisera from the two rabbits were pooled and subjected to peptide affinity purification, and the resulting anti-peptide polyclonal antibody showed specificity to this peptide by ELISA. It was then used as the primary antibody in immunohistochemistry on formalin-fixed human normal multi-tissue sections at concentrations of 2.5, 5, 10 and 20 µg/ml. At concentrations ranging from 5-20 µg/ml, the antibody showed largely negative staining in the liver and showed nuclear background staining in a variety of human tissues, including subsets of cells within the adrenal, colon, small intestine, kidney, lung, ovary, stomach, testis, spleen, prostate, tonsil, thyroid, and uterus. Faint cytoplasmic staining was observed at 10-20 µg/ml in renal tubules, and faint to moderate staining was observed in smooth muscle and mast cells. The antibody showed faint to moderate staining of prostatic secretions, but serum was negative. These results demonstrate that this anti-proalbumin antibody failed to stain in formalin-fixed tissues with a pattern consistent with the specific identification of proalbumin in human hepatocytes. Thus, it was concluded that an antibody raised against proalbumin is not suitable for use in IHC.

Example 2

Anti-Preproalbumin Antibody for Use in IHC Applications

Since an antibody raised against the proprotein form of albumin was not capable of specifically detecting the intracellular form of albumin (which includes preproalbumin and proalbumin) without background staining due to cross-reactivity to the secreted form albumin, it was next investigated whether an antibody raised against preproalbumin would be useful for IHC applications.

Preproalbumin Polypeptide Synthesis

In order to avoid cross-reactivity with albumin, but retain antigenicity to preproalbumin, a peptide with the last four amino acids of the leader sequence and proalbumin domain of preproalbumin were synthesized on a semi-automatic peptide synthesizer with a cysteine at the N-terminus (CSAYSRGVFRR; SEQ ID NO: 1). The peptide was purified to 90% purity and covalently conjugated to keyhole limpet hemocyanin (KLH), a carrier molecule. The polypeptide with carrier molecule is referred to herein as "preproalbumin-KLH." The peptide was also conjugated to bovine serum albumin (BSA) for use in immunoassays.

Anti-Preproalbumin Polyclonal Antibody Generation

After creation of the desired preproalbumin polypeptide, the next step of the procedure was to immunize a host with the polypeptide. Two pathogen-free New Zealand white rabbits were initially immunized subcutaneously with 0.4 mg of purified preproalbumin-KLH. Preproalbumin-KLH was emulsified in an equal volume of complete Freund's adjuvant, using 2 syringes connected through a luer fitting. In four 4-week increments, booster injections were given subcutaneously, using 0.1 to 0.3 mg preproalbumin-KLH diluted in Dulbecco's phosphate-buffered saline (D-PBS) and emulsified in incomplete Freund's adjuvant. Thirty ml whole blood was collected 12 days following the boosts, clotted and centrifuged at 3000 g for 15 minutes at 4° C., and the antiserum was frozen at −70° C.

Affinity Purification of Anti-Preproalbumin Polyclonal Antibody

An affinity column was constructed using the AMINO-LINK™ immobilization kit and 5 mg purified preproalbumin peptide was coupled to this affinity resin. Eight mg of IgG, purified from antiserum using a HITRAP™ 1 ml Protein A column, was loaded and washed on the affinity column with 50 mM tris, pH7.5, and eluted with 0.1 M Glycine-HCl, Ph 2.9. Column fractions were monitored for peak IgG by absorbance at 280 nm.

Enzyme Linked Immunosorbent Assay (ELISA)

Relative antibody production, specificity and background were determined by indirect ELISA. Briefly, the ELISA was performed in 96-well microtiter plates that were coated overnight with preproalbumin peptide at 1 µg/ml. The plates were then saturated with 2% BSA, followed by incubation with purified polyclonal antibody, antisera or negative controls (BSA and preimmunized rabbit serum) for 1 hour at room temperature. After washing with PBS-Tween, alkaline phosphatase conjugated goat anti-rabbit IgG was incubated for another hour, and the plates were washed again, and developed in the presence of substrate p-nitrophenyl phosphate (p-NPP). Color development was read at 405 nm in an ELSIA plate reader.

Immunohistochemistry

Immunohistochemical stains were performed on 5 µm formalin-fixed, paraffin-embedded tissues using the ABC method. Briefly, tissue sections were deparaffinized and then immersed in methanol containing 3% hydrogen peroxide to block endogenous peroxidase activity. The sections were then incubated with anti-preproalbumin (10 µg/ml) for one hour at room temperature and then anti-rabbit immunoglobulin conjugated with biotin, followed by streptavidin-peroxidase, for 30 minutes at room temperature. The immunoreactive products were visualized after immersion in a solution with diaminobenzidine. The slides were counterstained for nuclei with hematoxylin.

Preproalbumin Immunohistochemical Localization

The IHC results demonstrated that only hepatocytes and tumor cells with hepatocellular differentiation (i.e. hepatocellular carcinoma) show positive reactivity. The bile duct epithelium, stroma cells and endothelium within the liver exhibited no significant reactivity. Human tissues, including subsets of cells within the adrenal, colon, small intestine, kidney, lung, ovary, stomach, testis, spleen, prostate, tonsil, thyroid, and uterus, also showed no significant staining. Moreover, no significant background stain was observed. These results confirm that the anti-preproalbumin polyclonal antibody has no cross reactivity with albumin and the albumin molecules in the serum have no impact on the immunohistochemical staining of hepatocytes and hepatocellular carcinoma with anti-preproalbumin polyclonal antibody.

Example 3

Antibodies Specific for Intracellular/Membrane Immunoglobulin Light Chains

Normal mature B cells produce and export immunoglobulin to the cell surface as an antigen receptor. Normal plasma cells synthesize and secret immunoglobulin into the serum. The immunoglobulin molecule, a heterodimer comprising one light chain and one heavy chain molecule, is unique in each cell. The gene rearrangement process that generates the immunoglobulin molecule results in either a productive kappa gene or a productive lambda gene. The mechanics of the rearrangement process normally produce approximately twice as many kappa-bearing cells as lambda-bearing cells. This ratio is maintained in populations of normal or reactive B cells but is altered in malignant populations. In practice, whenever a B cell or plasma cell population exceeds the normal 2:1 ratio by four-fold (i.e. >85% kappa positive cells or roughly 65% lambda positive cells) malignant B cell lymphoma or malignant plasmacytoma/myeloma is diagnosed. However, light chain immunohistochemistry is complicated by an elevated background due to non-specific uptake of immunoglobulin by a variety of cells, or more often, staining of extracellular serum or stromal immunoglobulin molecules. Therefore, immunoglobulin light chain immunohistochemistry often results in a low signal with high background noise.

To overcome this obstacle, antibodies specific for the preprotein form of a kappa or lambda light chain can be generated. Exemplary kappa and lambda light chain preprotein sequences are known in the art, some of which are set forth herein as SEQ ID NOs: 3-39. A peptide comprising one of SEQ ID NOs: 3-39 is conjugated to a carrier, such as KLH. To generate polyclonal antibody specific for the preprotein form of a light chain, rabbits are immunized with the KLH-conjugated peptide according to the procedure described in Example 2. Relative antibody production, specificity and background can be determined by indirect ELISA. The polyclonal antibodies can then be used in IHC according to standard procedures (such as the method described in Example 2) to specifically detect the intracellular form of the light chain without background staining from the secreted form.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An immunohistochemical method for specific detection of an intracellular form of a protein in a biological sample, wherein the biological sample comprises a cell or tissue sample, the method comprising (i) contacting the sample with an antibody raised against a preproprotein or preprotein form of the protein, wherein the antibody specifically binds the intracellular form of the protein and does not bind a secreted form of the protein; and (ii) detecting by immunohistochemistry the presence of the antibody bound to the protein, thereby specifically detecting the intracellular form of the protein in the sample, wherein the protein is albumin, kappa light chain or lambda light chain.

2. The method of claim 1, wherein the protein is albumin.

3. The method of claim 1, wherein the protein is a kappa light chain.

4. The method of claim 1, wherein the protein is a lambda light chain.

5. The method of claim 1, wherein the antibody is a polyclonal antibody.

6. The method of claim 1, wherein the antibody is a monoclonal antibody.

7. The method of claim 1, wherein detecting the presence of the antibody bound to the protein comprises detecting a label conjugated to the antibody.

8. The method of claim 7, wherein the label is a fluorophore, enzyme or radioactive isotope.

9. The method of claim 1, wherein detecting the presence of the antibody bound to the protein comprises (i) contacting the sample with a secondary antibody specific for the preproprotein or preprotein antibody, wherein the secondary antibody is conjugated to a detectable label; and (ii) detecting the presence of the label.

10. The method of claim 9, wherein the label is a fluorophore, enzyme or radioactive isotope.

11. The method of claim 1, wherein detecting the presence of the antibody bound to the protein comprises (i) contacting the sample with a secondary antibody specific for the preproprotein or preprotein antibody, wherein the secondary antibody is conjugated to a first specific binding partner; (ii) contacting the sample with a detection molecule, wherein the detection molecule comprises a second specific binding partner fused to a detectable label; and (iii) detecting the presence of the label.

12. The method of claim 11, wherein the label is a fluorophore, enzyme or radioactive isotope.

13. The method of claim 12, wherein the enzyme is peroxidase.

14. The method of claim 11, wherein the first and second specific binding partners are biotin and avidin, or analogs or derivatives thereof.

15. An isolated antibody that specifically binds human preproalbumin, wherein the antibody does not bind a secreted form of albumin, and wherein the antibody was raised against a fragment of preproalbumin comprising the amino acid sequence of SAYSRGVFRR (amino acid residues 2-11 of SEQ ID NO: 1).

16. The isolated antibody of claim 15, wherein the antibody was raised against a peptide comprising the sequence of SEQ ID NO: 1.

17. The isolated antibody of claim 15, wherein the antibody was raised against a peptide consisting of the sequence of SEQ ID NO: 1.

18. The isolated antibody of claim 15, wherein the antibody is a polyclonal antibody.

19. The isolated antibody of claim 15, wherein the antibody is a monoclonal antibody, or an antigen-binding fragment thereof.

* * * * *

SEQUENCE LISTING

<160> NUMBER OF SEQ ID NOS: 40

<210> SEQ ID NO 1
<211> LENGTH: 11
<212> TYPE: PRT
<213> ORGANISM: Artificial Sequence
<220> FEATURE:
<223> OTHER INFORMATION: Synthetic preproalbumin peptide

<400> SEQUENCE: 1

Cys Ser Ala Tyr Ser Arg Gly Val Phe Arg Arg
1               5                   10

<210> SEQ ID NO 2
<211> LENGTH: 24
<212> TYPE: PRT
<213> ORGANISM: Homo sapiens

<400> SEQUENCE: 2

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 3
<211> LENGTH: 21
<212> TYPE: PRT
<213> ORGANISM: Homo sapiens

<400> SEQUENCE: 3

Met Asp Met Arg Val Leu Ala Gln Leu Leu Gly Leu Leu Leu Leu Cys
1               5                   10                  15

Phe Pro Gly Ala Cys
            20

<210> SEQ ID NO 4
<211> LENGTH: 20
<212> TYPE: PRT
<213> ORGANISM: Homo sapiens

<400> SEQUENCE: 4

Met Arg Ala Pro Thr Gln Leu Leu Gly Leu Leu Val Leu Trp Leu Pro
1               5                   10                  15

Gly Ala Arg Cys
            20

<210> SEQ ID NO 5
<211> LENGTH: 19
<212> TYPE: PRT
<213> ORGANISM: Homo sapiens

<400> SEQUENCE: 5

Met Gly Trp Ser Cys Ile Ile Leu Phe Leu Val Ala Thr Ala Thr Gly
1               5                   10                  15

Val His Ser

<210> SEQ ID NO 6
<211> LENGTH: 22
<212> TYPE: PRT
<213> ORGANISM: Homo sapiens

<400> SEQUENCE: 6

```
Thr Asp Val Arg Ala Pro Thr Gln Leu Leu Gly Leu Gly Leu Trp
1               5                   10                  15

Leu Pro Gly Ala Arg Cys
            20

<210> SEQ ID NO 7
<211> LENGTH: 22
<212> TYPE: PRT
<213> ORGANISM: Homo sapiens

<400> SEQUENCE: 7

Met Asp Met Arg Val Pro Ala Gln Leu Leu Gly Leu Leu Leu Trp
1               5                   10                  15

Leu Pro Gly Ala Lys Cys
            20

<210> SEQ ID NO 8
<211> LENGTH: 22
<212> TYPE: PRT
<213> ORGANISM: Homo sapiens

<400> SEQUENCE: 8

Met Glu Met Arg Val Pro Ala Gln Leu Leu Gly Leu Leu Leu Trp
1               5                   10                  15

Leu Arg Gly Ala Arg Cys
            20

<210> SEQ ID NO 9
<211> LENGTH: 22
<212> TYPE: PRT
<213> ORGANISM: Homo sapiens

<400> SEQUENCE: 9

Met Asp Met Arg Val Pro Ala Gln Leu Leu Gly Leu Leu Leu Trp
1               5                   10                  15

Phe Pro Gly Ser Arg Cys
            20

<210> SEQ ID NO 10
<211> LENGTH: 22
<212> TYPE: PRT
<213> ORGANISM: Homo sapiens

<400> SEQUENCE: 10

Met Asp Met Arg Val Pro Ala Gln Leu Leu Gly Leu Leu Leu Trp
1               5                   10                  15

Leu Pro Gly Ala Lys Cys
            20

<210> SEQ ID NO 11
<211> LENGTH: 22
<212> TYPE: PRT
<213> ORGANISM: Homo sapiens

<400> SEQUENCE: 11

Met Asp Met Arg Val Pro Ala Leu Leu Leu Gly Leu Leu Leu Trp
1               5                   10                  15

Leu Pro Gly Ala Lys Cys
            20

<210> SEQ ID NO 12
<211> LENGTH: 22
<212> TYPE: PRT
```

<213> ORGANISM: Homo sapiens

<400> SEQUENCE: 12

Met Asp Met Arg Val Pro Ala Gln Leu Leu Gly Leu Leu Leu Leu Trp
1               5                   10                  15
Leu Pro Gly Ala Arg Cys
            20

<210> SEQ ID NO 13
<211> LENGTH: 20
<212> TYPE: PRT
<213> ORGANISM: Homo sapiens

<400> SEQUENCE: 13

Met Arg Leu Pro Ala Gln Leu Leu Gly Leu Leu Met Leu Trp Val Ser
1               5                   10                  15
Gly Ser Ser Gly
            20

<210> SEQ ID NO 14
<211> LENGTH: 20
<212> TYPE: PRT
<213> ORGANISM: Homo sapiens

<400> SEQUENCE: 14

Met Arg Leu Pro Ala Gln Leu Leu Gly Leu Leu Met Leu Trp Val Pro
1               5                   10                  15
Gly Ser Ser Gly
            20

<210> SEQ ID NO 15
<211> LENGTH: 20
<212> TYPE: PRT
<213> ORGANISM: Homo sapiens

<400> SEQUENCE: 15

Met Arg Leu Pro Ala Gln Leu Leu Gly Leu Leu Met Leu Trp Ile Pro
1               5                   10                  15
Gly Ser Ser Gly
            20

<210> SEQ ID NO 16
<211> LENGTH: 20
<212> TYPE: PRT
<213> ORGANISM: Homo sapiens

<400> SEQUENCE: 16

Met Arg Leu Leu Ala Gln Leu Leu Gly Leu Leu Met Leu Trp Val Pro
1               5                   10                  15
Gly Ser Ser Gly
            20

<210> SEQ ID NO 17
<211> LENGTH: 20
<212> TYPE: PRT
<213> ORGANISM: Homo sapiens

<400> SEQUENCE: 17

Met Glu Ala Pro Ala His Val Leu Phe Leu Leu Leu Leu Trp Leu Pro
1               5                   10                  15
Glu Thr Ser Gly
            20

```
<210> SEQ ID NO 18
<211> LENGTH: 20
<212> TYPE: PRT
<213> ORGANISM: Homo sapiens

<400> SEQUENCE: 18

Met Gly Ser Gln Val His Leu Leu Ser Phe Leu Leu Trp Ile Ser
1               5                   10                  15

Asp Thr Arg Ala
            20

<210> SEQ ID NO 19
<211> LENGTH: 20
<212> TYPE: PRT
<213> ORGANISM: Homo sapiens

<400> SEQUENCE: 19

Met Val Leu Gln Thr Gln Val Phe Ile Ser Leu Leu Leu Trp Ile Ser
1               5                   10                  15

Gly Ala Tyr Gly
            20

<210> SEQ ID NO 20
<211> LENGTH: 22
<212> TYPE: PRT
<213> ORGANISM: Homo sapiens

<400> SEQUENCE: 20

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 21
<211> LENGTH: 22
<212> TYPE: PRT
<213> ORGANISM: Homo sapiens

<400> SEQUENCE: 21

Met Asp Met Arg Val Pro Ala Gln Leu Leu Gly Leu Leu Leu Leu Trp
1               5                   10                  15

Leu Arg Arg Val Arg Cys
            20

<210> SEQ ID NO 22
<211> LENGTH: 20
<212> TYPE: PRT
<213> ORGANISM: Homo sapiens

<400> SEQUENCE: 22

Met Val Leu Gln Thr Gln Val Phe Ile Ser Leu Leu Leu Trp Ile Ser
1               5                   10                  15

Gly Ala Tyr Gly
            20

<210> SEQ ID NO 23
<211> LENGTH: 22
<212> TYPE: PRT
<213> ORGANISM: Homo sapiens

<400> SEQUENCE: 23

Met Asp Met Arg Val Pro Ala Gln Leu Leu Gly Leu Leu Leu Leu Trp
1               5                   10                  15
```

```
Leu Ser Gly Ala Arg Tyr
            20

<210> SEQ ID NO 24
<211> LENGTH: 22
<212> TYPE: PRT
<213> ORGANISM: Homo sapiens

<400> SEQUENCE: 24

Met Asp Met Arg Val Pro Ala Gln Leu Leu Gly Leu Leu Leu Leu Trp
1               5                   10                  15

Leu Pro Gly Ala Arg Tyr
            20

<210> SEQ ID NO 25
<211> LENGTH: 20
<212> TYPE: PRT
<213> ORGANISM: Homo sapiens

<400> SEQUENCE: 25

Met Gln Val Pro Thr Gln Leu Leu Gly Leu Leu Val Leu Trp Leu Pro
1               5                   10                  15

Gly Ala Arg Cys
            20

<210> SEQ ID NO 26
<211> LENGTH: 22
<212> TYPE: PRT
<213> ORGANISM: Homo sapiens

<400> SEQUENCE: 26

Met Asp Met Arg Ala Pro Ala Gln Leu Leu Gly Leu Leu Leu Leu Trp
1               5                   10                  15

Leu Pro Asp Thr Arg Cys
            20

<210> SEQ ID NO 27
<211> LENGTH: 12
<212> TYPE: PRT
<213> ORGANISM: Homo sapiens

<400> SEQUENCE: 27

Gly Leu Leu Pro Ser Trp Phe Pro Gly Thr Arg Ser
1               5                   10

<210> SEQ ID NO 28
<211> LENGTH: 20
<212> TYPE: PRT
<213> ORGANISM: Homo sapiens

<400> SEQUENCE: 28

Met Glu Thr Pro Ala Gln Leu Leu Phe Leu Leu Leu Leu Trp Leu Pro
1               5                   10                  15

Asp Thr Thr Gly
            20

<210> SEQ ID NO 29
<211> LENGTH: 20
<212> TYPE: PRT
<213> ORGANISM: Homo sapiens

<400> SEQUENCE: 29

Met Arg Cys Ser Pro His Phe Leu Glu Leu Leu Val Phe Trp Ile Leu
```

-continued

```
                1               5                  10                  15

Glu Val Ser Gly
            20

<210> SEQ ID NO 30
<211> LENGTH: 19
<212> TYPE: PRT
<213> ORGANISM: Homo sapiens

<400> SEQUENCE: 30

Met Ala Gly Phe Pro Leu Leu Leu Thr Leu Leu Thr His Cys Ala Gly
1               5                  10                  15

Ser Trp Ala

<210> SEQ ID NO 31
<211> LENGTH: 19
<212> TYPE: PRT
<213> ORGANISM: Homo sapiens

<400> SEQUENCE: 31

Met Thr Cys Ser Pro Leu Leu Leu Thr Leu Leu Ile His Cys Thr Gly
1               5                  10                  15

Ser Trp Ala

<210> SEQ ID NO 32
<211> LENGTH: 19
<212> TYPE: PRT
<213> ORGANISM: Homo sapiens

<400> SEQUENCE: 32

Met Ala Trp Thr Pro Leu Leu Leu Leu Phe Leu Ser His Cys Thr Gly
1               5                  10                  15

Pro Leu Ser

<210> SEQ ID NO 33
<211> LENGTH: 20
<212> TYPE: PRT
<213> ORGANISM: Homo sapiens

<400> SEQUENCE: 33

Met Thr Trp Thr Pro Leu Leu Phe Leu Thr Leu Leu His Cys Thr
1               5                  10                  15

Gly Ser Leu Ser
            20

<210> SEQ ID NO 34
<211> LENGTH: 19
<212> TYPE: PRT
<213> ORGANISM: Homo sapiens

<400> SEQUENCE: 34

Met Ala Trp Thr Pro Leu Phe Leu Phe Leu Thr Cys Cys Pro Gly
1               5                  10                  15

Ser Asn Ser

<210> SEQ ID NO 35
<211> LENGTH: 15
<212> TYPE: PRT
<213> ORGANISM: Homo sapiens

<400> SEQUENCE: 35

Pro Leu Ser Ser Val Leu Leu Thr Leu Cys Thr Gly Ser Glu Ala
```

```
<210> SEQ ID NO 36
<211> LENGTH: 19
<212> TYPE: PRT
<213> ORGANISM: Homo sapiens

<400> SEQUENCE: 36

Met Ala Trp Thr Val Leu Leu Leu Gly Leu Leu Ser His Cys Thr Gly
1               5                   10                  15

Ser Val Thr

<210> SEQ ID NO 37
<211> LENGTH: 19
<212> TYPE: PRT
<213> ORGANISM: Homo sapiens

<400> SEQUENCE: 37

Met Ala Trp Thr Pro Leu Trp Leu Thr Leu Phe Thr Leu Cys Ile Gly
1               5                   10                  15

Ser Val Val

<210> SEQ ID NO 38
<211> LENGTH: 20
<212> TYPE: PRT
<213> ORGANISM: Homo sapiens

<400> SEQUENCE: 38

Met Ala Trp Thr Pro Leu Trp Leu Thr Leu Phe Thr Leu Cys Ile Gly
1               5                   10                  15

Ser Val Val Ser
            20

<210> SEQ ID NO 39
<211> LENGTH: 19
<212> TYPE: PRT
<213> ORGANISM: Homo sapiens

<400> SEQUENCE: 39

Met Ala Trp Ala Pro Leu Leu Leu Thr Leu Leu Ala His Cys Thr Asp
1               5                   10                  15

Cys Trp Ala

<210> SEQ ID NO 40
<211> LENGTH: 7
<212> TYPE: PRT
<213> ORGANISM: Homo sapiens

<400> SEQUENCE: 40

Arg Gly Val Phe Arg Arg Cys
1               5
```